(12) United States Patent
Tani et al.

(10) Patent No.: US 8,517,920 B2
(45) Date of Patent: Aug. 27, 2013

(54) IMAGING-DEVICE DRIVING UNIT, ELECTRONIC ENDOSCOPE, AND ENDOSCOPE SYSTEM

(75) Inventors: Nobuhiro Tani, Tokyo (JP); Noriko Iriyama, Saitama (JP)

(73) Assignee: Hoya Corporation, Tokyo (JP)

( * ) Notice: Subject to any disclaimer, the term of this patent is extended or adjusted under 35 U.S.C. 154(b) by 967 days.

(21) Appl. No.: 12/327,894

(22) Filed: Dec. 4, 2008

(65) Prior Publication Data
US 2009/0149705 A1  Jun. 11, 2009

(30) Foreign Application Priority Data
Dec. 5, 2007  (JP) .................. 2007-315071

(51) Int. Cl.
*A61B 1/04* (2006.01)
(52) U.S. Cl.
USPC ............................................. 600/118
(58) Field of Classification Search
USPC ................. 600/118; 396/17; 348/69
See application file for complete search history.

(56) References Cited

U.S. PATENT DOCUMENTS

| | | | |
|---|---|---|---|
| 7,042,487 B2 | 5/2006 | Nakashima | |
| 2002/0021356 A1 | 2/2002 | Nakashima | |
| 2004/0162492 A1* | 8/2004 | Kobayashi | 600/476 |
| 2008/0002043 A1* | 1/2008 | Inoue et al. | 348/296 |
| 2008/0018734 A1 | 1/2008 | Iriyama | |
| 2008/0097151 A1 | 4/2008 | Inoue | |
| 2008/0143826 A1 | 6/2008 | Shibasaki | |
| 2008/0200764 A1 | 8/2008 | Okada | |
| 2008/0232131 A1 | 9/2008 | Suda | |
| 2009/0118600 A1* | 5/2009 | Ortiz et al. | 600/306 |

FOREIGN PATENT DOCUMENTS

| | | |
|---|---|---|
| JP | 63-264717 | 11/1988 |
| JP | 2002-58642 | 2/2002 |
| JP | 2002-058642 A | 2/2002 |
| JP | 2003-38428 | 2/2003 |
| JP | 2007-19706 | 1/2007 |
| JP | 2007105236 A * | 4/2007 |

OTHER PUBLICATIONS

Chinese Office Action, dated Sep. 23, 2011, for the corresponding Chinese Application (together with an English translation thereof).
English language Abstract of JP 2002-58642, Feb. 26, 2002.
U.S. Appl. No. 12/327,892 to Tani et al., which was filed Dec. 4, 2008.
U.S. Appl. No. 12/327,895 to Tani et al., which was filed Dec. 4, 2008.
Japanese Office Action, dated Jul. 31, 2012, (together with an English translation thereof) from Japanese Patent Office (JPO) for corresponding Japanese patent application.

* cited by examiner

*Primary Examiner* — Clayton E Laballe
*Assistant Examiner* — Noam Reisner
(74) *Attorney, Agent, or Firm* — Greenblum & Bernstein, P.L.C.

(57) ABSTRACT

An imaging-device driving unit comprising a detector and an exposure controller is provided. The imaging-device driving unit controls a CMOS imaging device amounted in an endoscope. The detector detects the pattern of emitted illumination light. The illumination light is emitted by a light source. The illumination light is shone on a subject. The CMOS imaging device is ordered to capture an optical image of the subject. The exposure controller orders the CMOS imaging device to perform the global exposure and the line exposure when the patterns of emitted illumination light detected by the detector are the first and second patterns, respectively.

4 Claims, 6 Drawing Sheets

IMAGING-DEVICE DRIVING UNIT, ELECTRONIC ENDOSCOPE, AND ENDOSCOPE SYSTEM

BACKGROUND OF THE INVENTION

1. Field of the Invention

The present invention relates to an imaging-device driving unit which drives an imaging device according to the emission pattern of illumination light.

2. Description of the Related Art

An electronic endoscope having an imaging device at a head end of an insertion tube is known. By transmitting illumination light emitted by the light source to the head end of an insertion tube through an optical fiber, a subject in a dark area such as one inside the body, or an internal mechanism, can be photographed and/or filmed.

An image with a special visible effect can be displayed by using a special illumination method on a subject. For example, in a known technique, a subject is illuminated by pulses of light generated by pulse emission. By filming the vocal cords illuminated by pulses of light at a frequency adjusted to be nearly the same as the vibration of the vocal cords, an image of the quickly vibrating vocal cords, can be generated such that they appear to vibrate slowly.

If a user desires to observe a rapidly moving subject, then the user will usually select pulsed light. Accordingly, it is preferable for all the pixels to receive light simultaneously in order to capture an optical image of the subject using pulsed light illumination. On the other hand, if a user desires to observe a still or slowly moving subject, the user will select continuous light. Accordingly, when using continuous light illumination, it is preferable to generate an image signal in which noise in the captured image is reduced.

In order to film a subject with global exposure and also reduce noise, prior electronic endoscope has typically employed CCD imaging devices. However, some problems include high manufacturing cost of the CCD imaging device, high voltage requirement to drive the CCD imaging device, and requirement of many signal lines in a CCD imaging device.

To solve such problems, Japanese Unexamined Patent Publication No. 2002-58642 proposes that a CMOS imaging device with its lower power consumption and manufacturing cost than a CCD imaging device, be used in an electronic endoscope. However, there is the problem of a higher signal-to-noise ratio in the image signal generated by a CMOS imaging device when global exposure is used. Accordingly, when a CMOS imaging device is used to generate an image signal with global exposure, noise in a displayed image becomes conspicuous when a subject is illuminated by continuous light as compared to pulsed light.

SUMMARY OF THE INVENTION

Therefore, an object of the present invention is to provide an imaging-device driving unit that adequately drives a CMOS imaging device according to the temporal pattern of emitted illumination light, such as that of pulsed or continuously emitted light.

According to the present invention, an imaging-device driving unit comprising a detector and an exposure controller is provided. The imaging-device driving unit controls a CMOS imaging device mounted in an endoscope. The detector detects the pattern of emitted illumination light. The illumination light is emitted by a light source. The illumination light is shone on a subject. The CMOS imaging device is ordered to capture an optical image of the subject. The exposure controller orders the imaging device to perform the global exposure and the line exposure when the patterns of emitted illumination light detected by the detector are the first and second patterns, respectively.

Further, the light source emits pulsed light and continuous light in the first and second patterns, respectively.

BRIEF DESCRIPTION OF THE DRAWINGS

The objects and advantages of the present invention will be better understood from the following description, with reference to the accompanying drawings in which.

DESCRIPTION OF THE PREFERRED EMBODIMENTS

Figure 1:
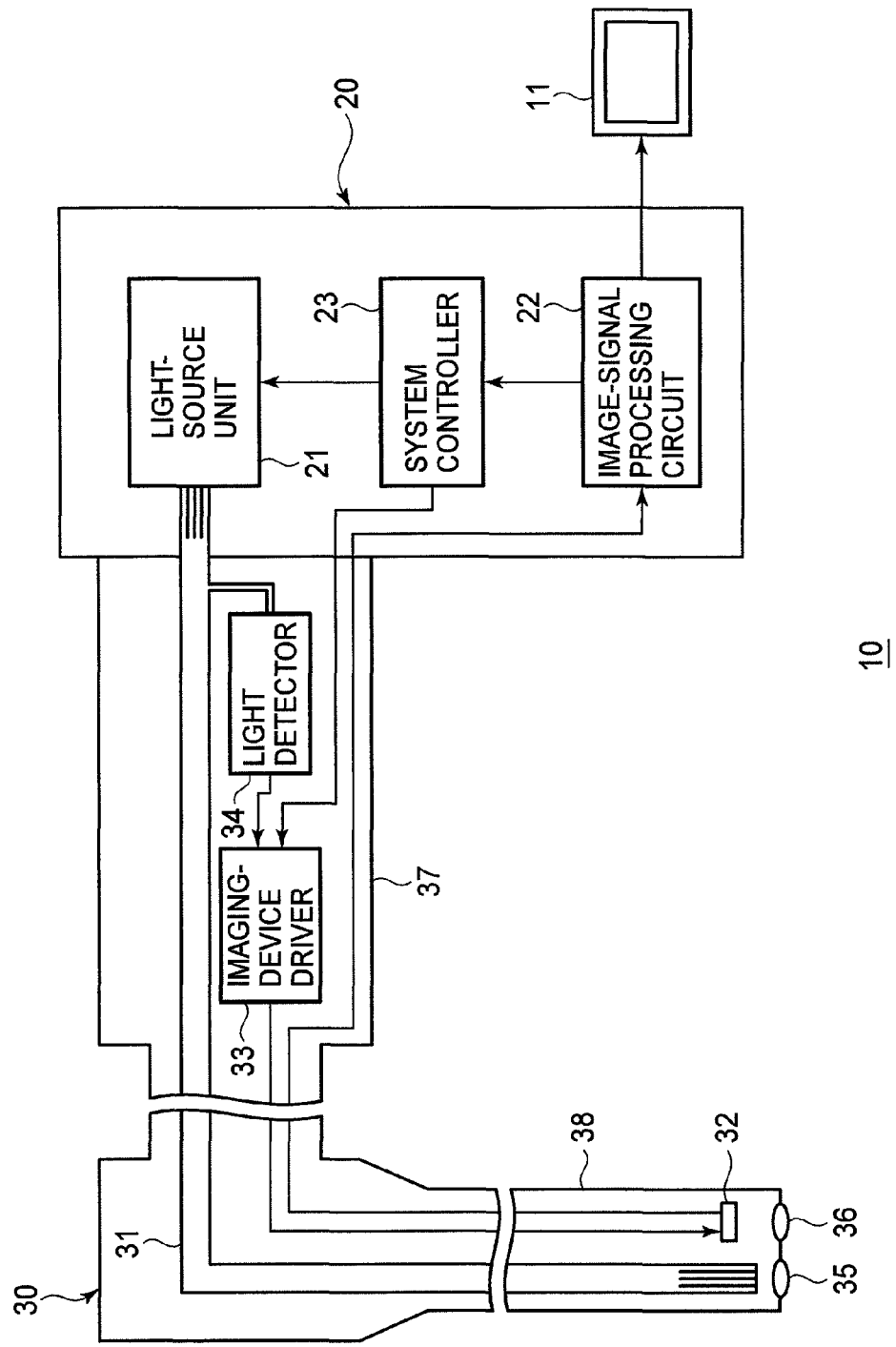
FIG. 1 is a block diagram showing the internal structure of an endoscope system having an imaging-device driving unit of an embodiment of the present invention.

The present invention is described below with reference to the embodiments shown in the drawings.

In FIG. 1, an endoscope system 10 comprises an endoscope processor 20, an electronic endoscope 30, and a monitor 11. The endoscope processor 20 is connected to the electronic endoscope 30 and the monitor 11.

The endoscope processor 20 emits illumination light to illuminate a required object. The illuminated object is photographed and/or filmed by the electronic endoscope 30, and then the electronic endoscope 30 generates an image signal. The image signal is sent to the endoscope processor 20.

The endoscope processor 20 carries out predetermined signal processing on the received image signal. The image signal, having undergone predetermined signal processing is sent to the monitor 11, where an image corresponding to the received image signal is displayed.

The endoscope processor 20 comprises a light-source unit 21, an image-signal processing circuit 22, a system controller 23, and other components. As described below, the light-source unit 21 emits the illumination light for illuminating a desired object toward the incident end of light guide 31. In addition, as described below, the image-signal processing circuit 22 carries out predetermined signal processing on the image signal. In addition, the system controller 23 controls the operations of all components of the endoscope system 10.

By connecting the endoscope processor 20 to the connector 37 of the electronic endoscope 30, the light-source unit 21 and a light-guide 31 mounted in the electronic endoscope 30 become optically connected. In addition, by connecting the endoscope processor 20 to the connector 37, electrical connections are made between the image-signal processing circuit 22 and an imaging device 32 mounted in the electronic endoscope 30, and between the system controller 23 and an imaging device driver 33 mounted in the electronic endoscope 30.

Figure 2:
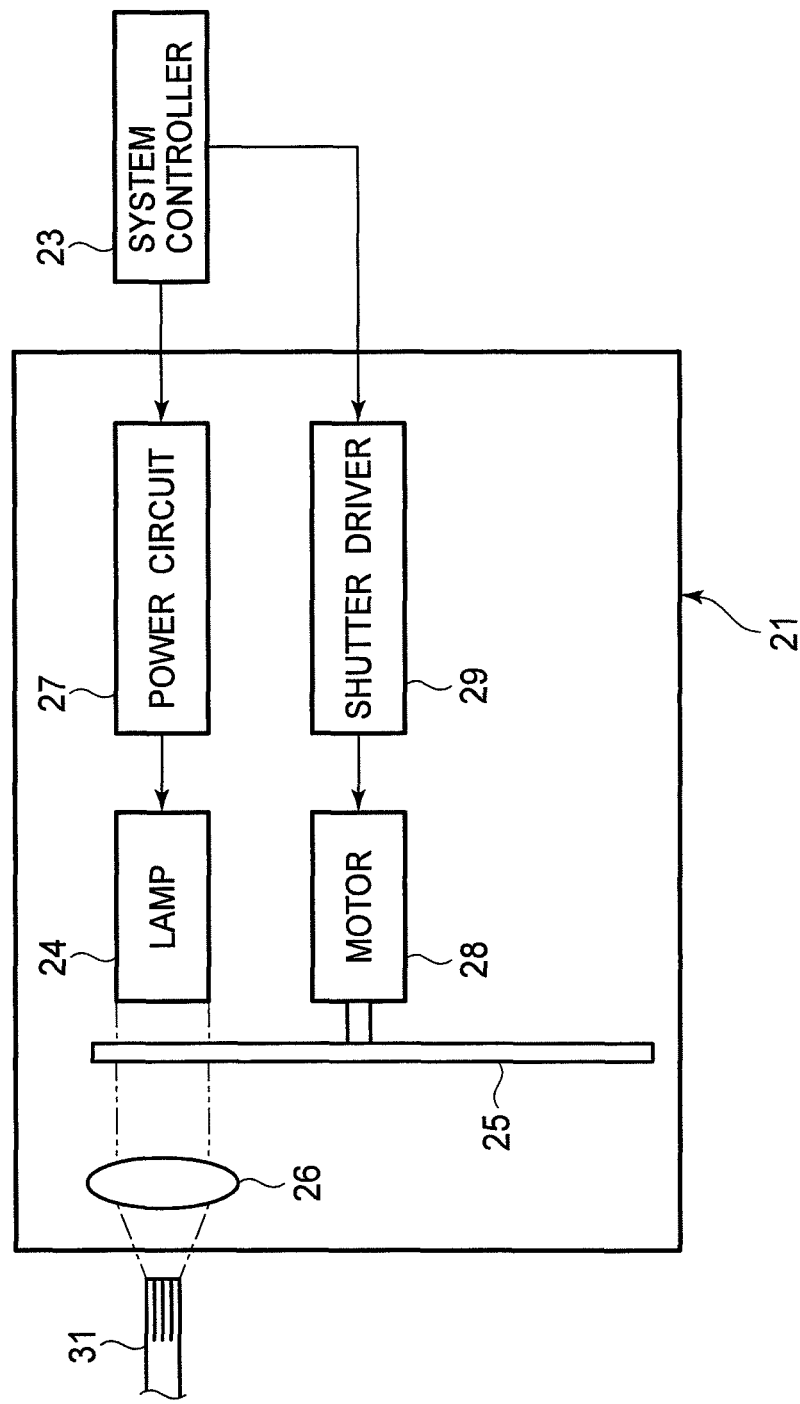
FIG. 2 is a block diagram showing the internal structure of a light-source unit.

As shown in FIG. 2, the light-source unit 21 comprises a lamp 24, a rotary shutter 25, a condenser lens 26, a power circuit 27, a motor 28, a shutter driver 29, and other components.

The lamp 24 is, for example, a xenon lamp or halogen lamp, and emits white light. The rotary shutter 25 and the condenser lens 26 are mounted on an optical path of white light from the lamp 24 to the incident end of the light guide 31.

The rotary shutter 25 has a circular plate shape and has an aperture area and a blocking area. When white light should be emitted from the light source unit 21, the aperture area is inserted into the optical path of white light. On the other hand, when the emission of white light should be suspended, the blocking area is inserted into the optical path of white light, blocking white light. The motor 28 makes the rotary shutter 25 rotate. By adjusting the rotation of the rotary shutter 25, the illumination light switches between emission and suppression. In addition, by holding the aperture in the optical path, white light is continuously emitted from the light-source unit 21.

The motor 25 is driven by the shutter driver 29. The shutter driver 29 is controlled by the system controller 23.

White light emitted by the light-source unit 21 is condensed by the condenser lens 26, and is directed to the incident end of the light guide 31. The power circuit 27 supplies the lamp 24 with power. The system controller 23 switches power supply to the lamp 24 from the power circuit 27 to power the lamp 24 on and off.

Next, the structure of the electronic endoscope 30 is explained in detail. As shown in FIG. 1, the electronic endoscope 30 comprises the light guide 31, the imaging device 32, an imaging device driver 33, a light detector 34, a diffuser lens 35, a subject lens 36, and other components.

The light guide 31 is a bundle of optical fibers, and branches off within the connector 37. One branch is optically connected to the light detector 34. The other branch, hereinafter referred to as exit end, is mounted at the head end of the insertion tube 37 of the electronic endoscope 30. The bundled end opposite both branches sticks out of the connector 37, and is optically connected to the light-source unit 21.

As described above, white light emitted by the light-source unit 21 arrives at the incident end of the light guide 31. The light is then transmitted to the light detector and the exit end.

The light detector 34 determines the light-source unit 21 is in pulse emission or continuous emission based on the light transmitted by the light guide 31. In pulse emission, the light-source unit 21 emits pulsed light by alternating repeatedly between the emission and the suspension of light. In continuous emission, the light-source unit 21 continuously emits light. The determined emission type is communicated to the imaging device driver 33. In the case of pulse emission, the imaging device driver 33 sends the global exposure order signal to the imaging device 32. On the other hand, in the case of continuous emission, the imaging device driver 33 sends the line exposure order signal to the imaging device 32. Such operations of the imaging device driver 33 are controlled by the system controller 23.

The light transmitted to the exit end illuminates a peripheral area near the head end of an insertion tube 38 through a diffuser lens 35.

An optical image of reflection light of the subject illuminated by white light reaches a light-receiving surface of the imaging device 32 through the subject lens 35. The imaging device driver 33 drives the imaging device 32 to generate an image signal corresponding to the optical image reaching the light-receiving surface.

Figure 3:
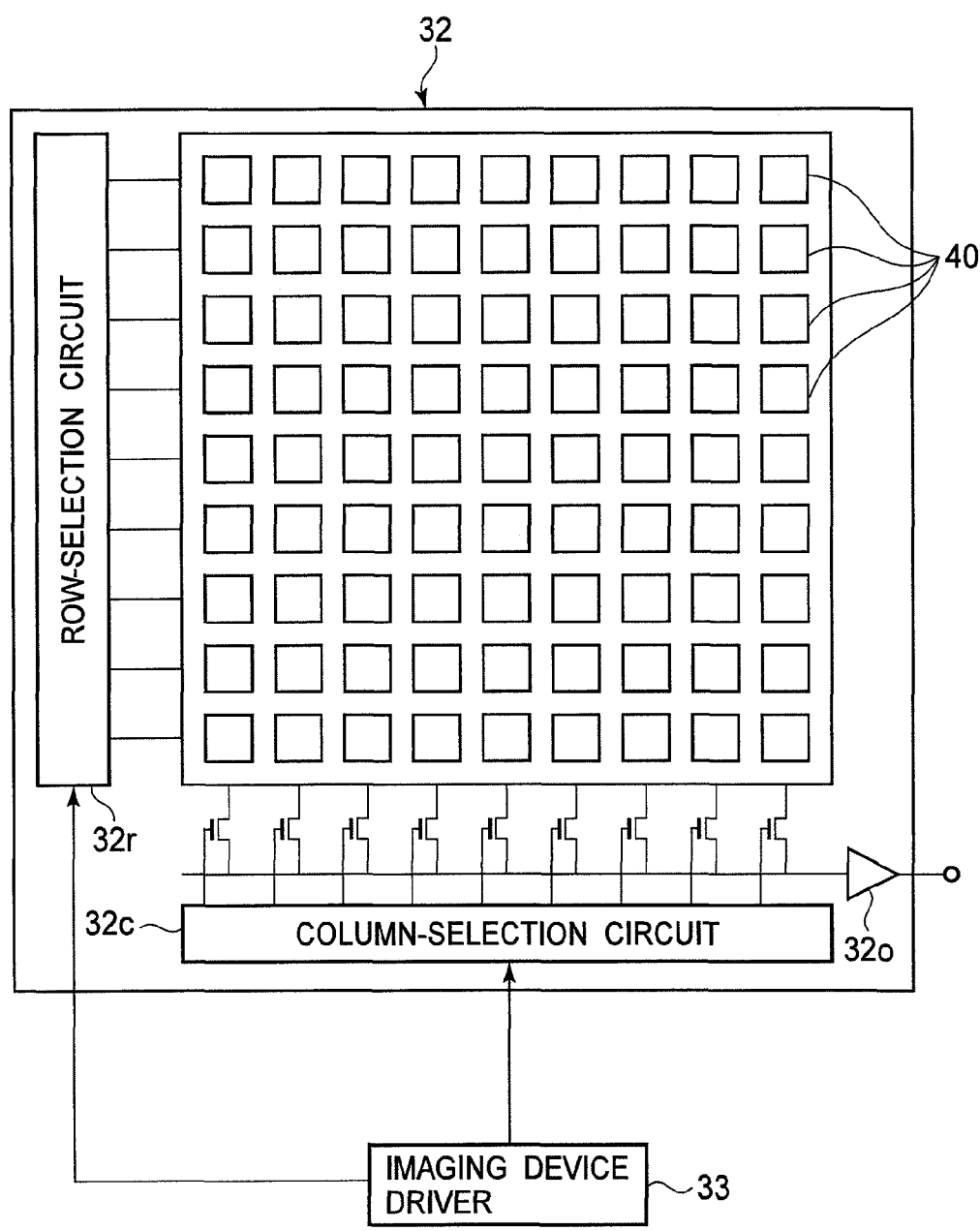
FIG. 3 is a block diagram showing the structure of an imaging device.

The imaging device 32 is a CMOS imaging device. As shown in FIG. 3, a plurality of pixels 40 are arranged in matrix on the light-receiving surface of the imaging device 32. Each pixel 40 generates a pixel signal according to the amount of light received by the pixel 40. The pixel signals are output one by one in order via the output block 32o. The image signal comprises a plurality of pixel signals generated by all the pixels 40 on the entire light-receiving surface. A pixel 40 that should be ordered to output the pixel signal is selected by a row-selection circuit 32r and a column-selection circuit 32c.

Figure 4:
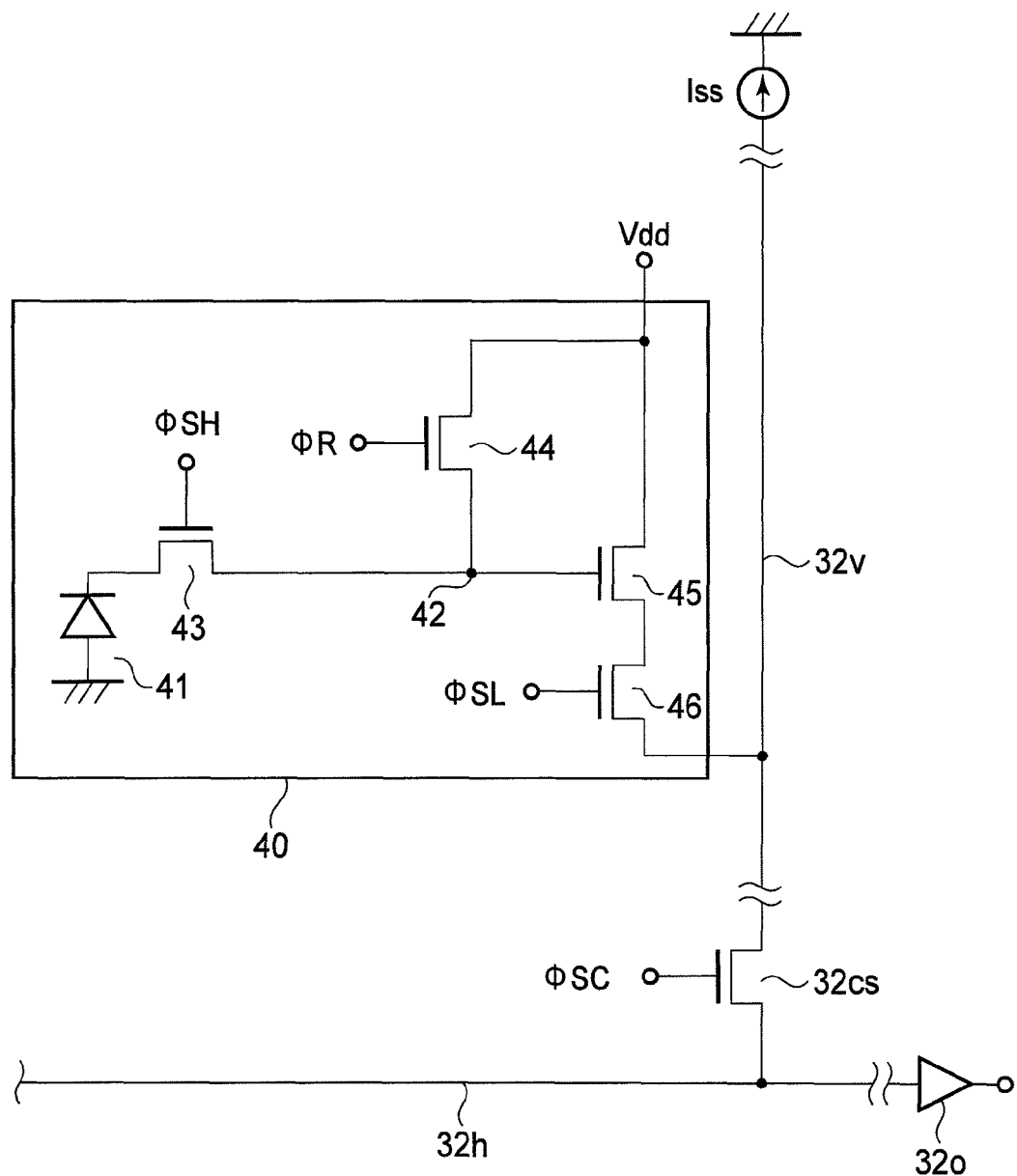
FIG. 4 is a circuit diagram showing the internal structure of a pixel.

The internal structure of each pixel 40 is explained below using FIG. 4. The pixel 40 comprises a photodiode (PD) 41, a floating diffusion (FD) 42, a shutter transistor 43, a reset transistor 44, an amplification transistor 45, and a row-selection transistor 46.

A signal charge is generated according to the amount of light received and stored by photoelectric conversion of the PD 41. The stored signal charge is transmitted to the FD 42 when the shutter transistor is switched on. The FD 42 is a capacitor, of which electrical potential varies according to stored signal charge.

A shutter signal line (not depicted) is mounted along each row of pixels 40. The shutter signal line is connected to shutter transistors 43 in all the pixels 40 arranged in a given row. A shutter signal, hereinafter referred to as φSH, is sent to all shutter signal lines. The φSH has high and low states. The φSHs, which are sent to each row of the shutter signal line, is set to the high state at different times for each row. When the φSH is set to the high state, the shutter transistor 43 is switched on, and consequently, the shutter transistor 43 becomes conductive.

When the reset transistor 44 is switched on, the FD 42 is reset. Then, the signal charge stored in the FD 42 is swept to a power source, hereinafter referred to as Vdd. Then, the electrical potential of the FD 42 is reset to an electrical potential of the Vdd.

A reset signal line (not depicted) is mounted along each row of pixels 40. The reset signal line is connected to reset transistors 44 in all the pixels 40 arranged in a given row. A reset signal, hereinafter referred to as φR, is sent to all reset signal lines. The φR has high and low states. The φRs, which are sent to each row of the reset signal line, is set to the high state at different times for a row. While the φR is set to the high state, the reset transistor 44 is switched on, making the reset transistor 44 conductive.

The amplifier transistor 45 outputs a pixel signal to the row-selection transistor 46 according to the electrical potential of the FD 42. When the row-selection transistor is switched on, the pixel signal is output to a vertical output line 32v.

A vertical output line 32v is mounted along every column of pixels 40. All pixels arranged in a given column are connected to the same adjacent vertical output line 32v. By separately switching on each of the row-selection transistors 46, pixel signals can be output separately from pixels 40 connected to the same vertical output lines 32v.

A row-selection signal line (not depicted) is mounted along each row of pixels 40. The row signal line is connected to row-selection transistor 46 in all the pixels 40 arranged in a given row. A row-selection signal, hereinafter referred to as φSL, is sent to all row-selection signal lines. The φSL has high and low states. The φSLs, which are sent to each row of the row-selection signal line, is set to the high state at different times for each row. While the φSL is set to the high state, the row-selection transistor 46 is switched on, making the row-selection transistor 46 conductive.

The vertical output lines 32v are connected to the horizontal output line 32h via column-selection transistors 32cs. By switching on the column-selection transistors 32cs one by one in order, the pixel signals output to the vertical output lines 32v of all columns can be output separately to the image-signal processing circuit 22 via the horizontal output line 32h and the output block 32o.

Column selection signals, hereinafter referred to as φSC, are transmitted separately to the column-selection transistors 32cs. While the φSC is set to the high state, the column selection transistor 32cs is switched on, making the column selection transistor 32cs conductive.

The row-selection circuit 32r outputs the φSH, φR, and φSL to the shutter signal line, the reset signal line, and the row-selection signal line to control the switching operations of the shutter transistor 43, the reset transistor 44, and the row-selection transistor 46. The column-selection circuit 32c outputs the φSC to the column selection transistor 32cs to control the switching operation of the column selection transistor 32cs.

The row-selection circuits 32r and the column-selection circuit 32c control the switching operations on the basis of signals used for driving the imaging device, such as a clock signal, transmitted from the imaging device driver 33 (exposure controller).

As described in detail below, when the row-selection circuit 32r and the column-selection circuit 32c receive the global exposure order signal, the row and column-selection circuits 32r and 32c carry out the switching operations of the shutter transistor 43, the reset transistor 44, the row selection transistor 46, and the column-selection transistor 32cs so that the global exposure is carried out. On the other hand, when the row and column-selection circuits 32r and 32c receive the line exposure order signal, the row and column-selection circuits 32r and 32c carry out the switching operations of the shutter transistor 43, the reset transistor 44, the row selection transistor 46, and the column-selection transistor 32cs so that the line exposure is carried out.

The operations of the imaging device 32 used to generate an image signal are described below.

A frame signal which is cyclically switched between high and low states is transmitted from the system controller 22 to the imaging device driver 33. While the frame signal is kept in the high or low state, pixel signals are generated by all the pixels 40 on the entire light-receiving surface of the imaging device 32, and are then output.

Figure 5:
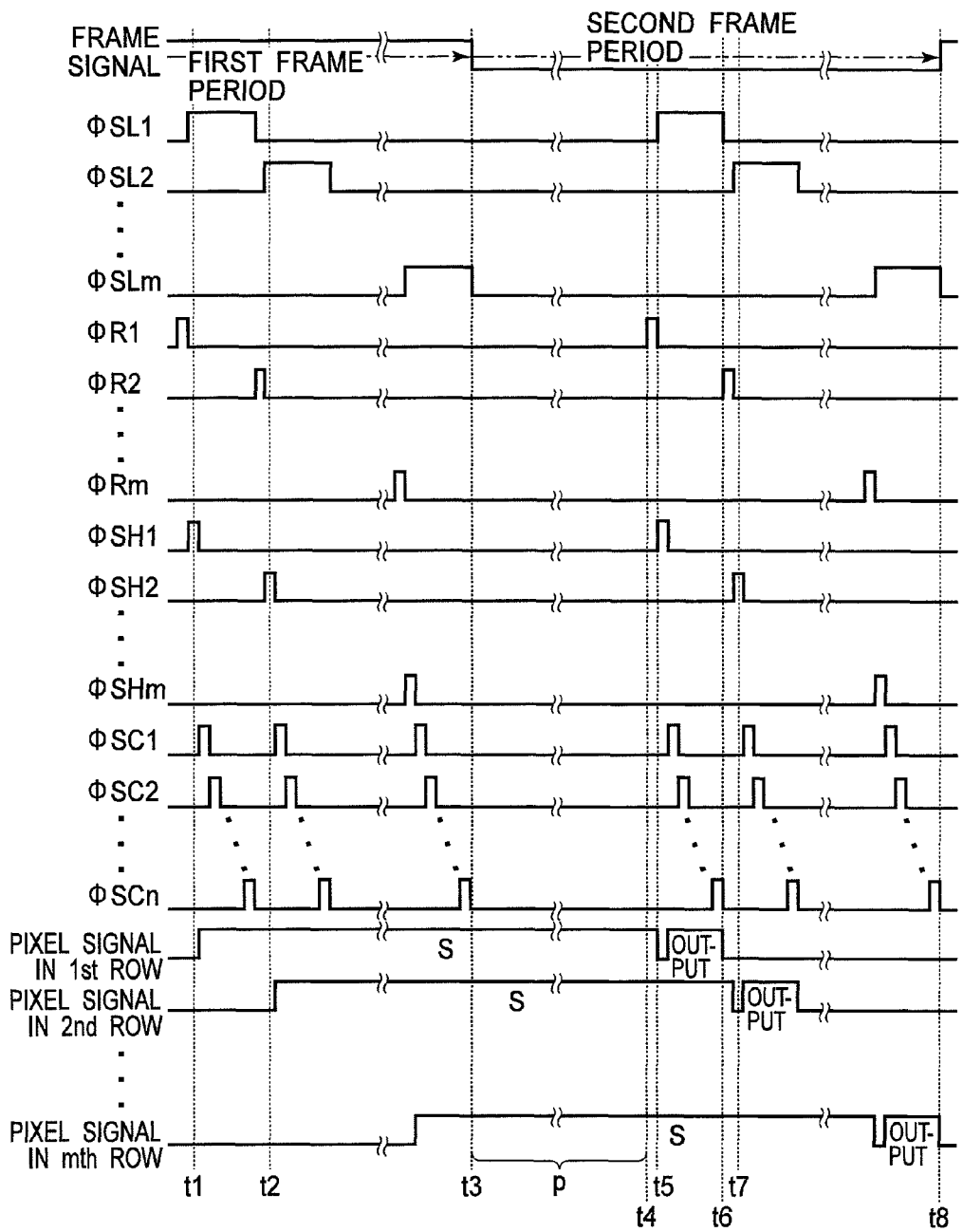
FIG. 5 is a timing chart illustrating the timing used to drive the imaging device to generate an image signal with line exposure.

The operations of the imaging device 32 used to generate an image signal by line exposure are described below with reference to FIG. 5.

At time t1 in the first period, the φSH for the first row, hereinafter referred to as φSH1, is set to the high state, and then, the signal charges stored by the PDs 41 are transmitted to the FDs 42 in the pixels 40 in the first row. After the transmission of the signal charges and after the φSH1 is set to the low state, the PDs in all the pixels 40 in the first row start to generate and store signal charges.

At time t2 after time t1 in the first frame period, the φSH for the second row, hereinafter referred to as φSH2, is set to the high state, and then, the signal charges stored by the PDs 41 are transmitted to the FDs 42 in the pixels 40 in the second row. After the transmission of the signal charges and after the φSH2 is set to the low state, the PDs 41 in all the pixels 40 in the second row start to generate and store signal charges.

Since then, by ordering the φSH for each row set to the low state once having been set to the high state one by one in order, the PDs 41 in all the pixels 40 in each row start to generate and store signal charges.

After outputting the pixel signals from the last row for the first frame period, the first frame period comes to an end. Then, the second frame period starts (see time "t3"). At time t4 a period has passed predetermined as sufficient for storing enough signal charges in the PDs 41 (see "p"), the φR for the first row, hereinafter referred to as φR1, is set to the high state, and then the reset transistors 44 in all the pixels in the first row are switched on. By switching on the reset transistors 44, the FDs 42 are reset, and then, signal charges stored by the FDs 42 are swept to the Vdd.

At time t5 after resetting the FDs 42 in the pixels 40 in the first row, the φSL for the first row, hereinafter referred to as φSL1, is set to the high state, and the row-selection transistors 46 in all the pixels 40 in the first row are switched on. By switching on the row-selection transistors 46 in the pixels 40 in the first row, the pixels signals are ready for output from the pixels 40 in the first row. As described below, the φSL1 is kept in the high state until the output of pixel signals from all the pixels in the first row has finished.

In addition, soon after time t5, the φSH1 is set to the high state, and then, the signal charge that is generated and stored by the PDs 41 between time t1 and time t5 (refer to "S" in the row of "pixel signal in the first row") are transferred to the FDs 42.

When the transfer of the signal charge to the FDs 42 completes, the φSCs for the first to nth columns, hereinafter referred to as φSC1 to φSCn, are set to the high state one by one in order, and then the column-selection transistors 32cs in the first to nth columns are switched on one by one in order. Incidentally, n is a positive integer. Accordingly, all the pixel signals between the first and nth columns in the first row are output from the imaging device 32 in order.

At time t6 after outputting the pixel signal generated by the pixel in the nth column in the first row, the φSL1 is set to the low state. Subsequently, the φR for the second row, hereinafter referred to as φR2, is set to the high state. Then, the FDs 42 in the pixels 40 in the second row are reset, as in the first row. After resetting the FDs 42, the φSL for the second row, hereinafter referred to as φSL2, is set to the high state, and then the pixel signals are ready for output from the pixels 40 in the second row.

At time t7 soon after the φSL2 is set to the high state, the φSH2 is set to the high state, and then, the signal charge that is generated and stored by the PDs 41 between time t2 and time t7 (refer to "S" in the row of "pixel signal in the second row") are transferred to the FDs 42, as in the first row. In addition, all the pixel signals in the first row are output from the imaging device 32 in order, as in the first row.

Since then, the pixel signals in the third to mth row, which is the last row, are output in order, as in the first and second rows. At time t8 after finishing the output of the pixel signals in the mth row, the frame signal is set to the high state. When the frame signal is switched between high and low states, the generation of a frame's worth of an image signal corresponding to a captured optical image is finished, and then, the subsequent frame starts to be generated.

Figure 6:
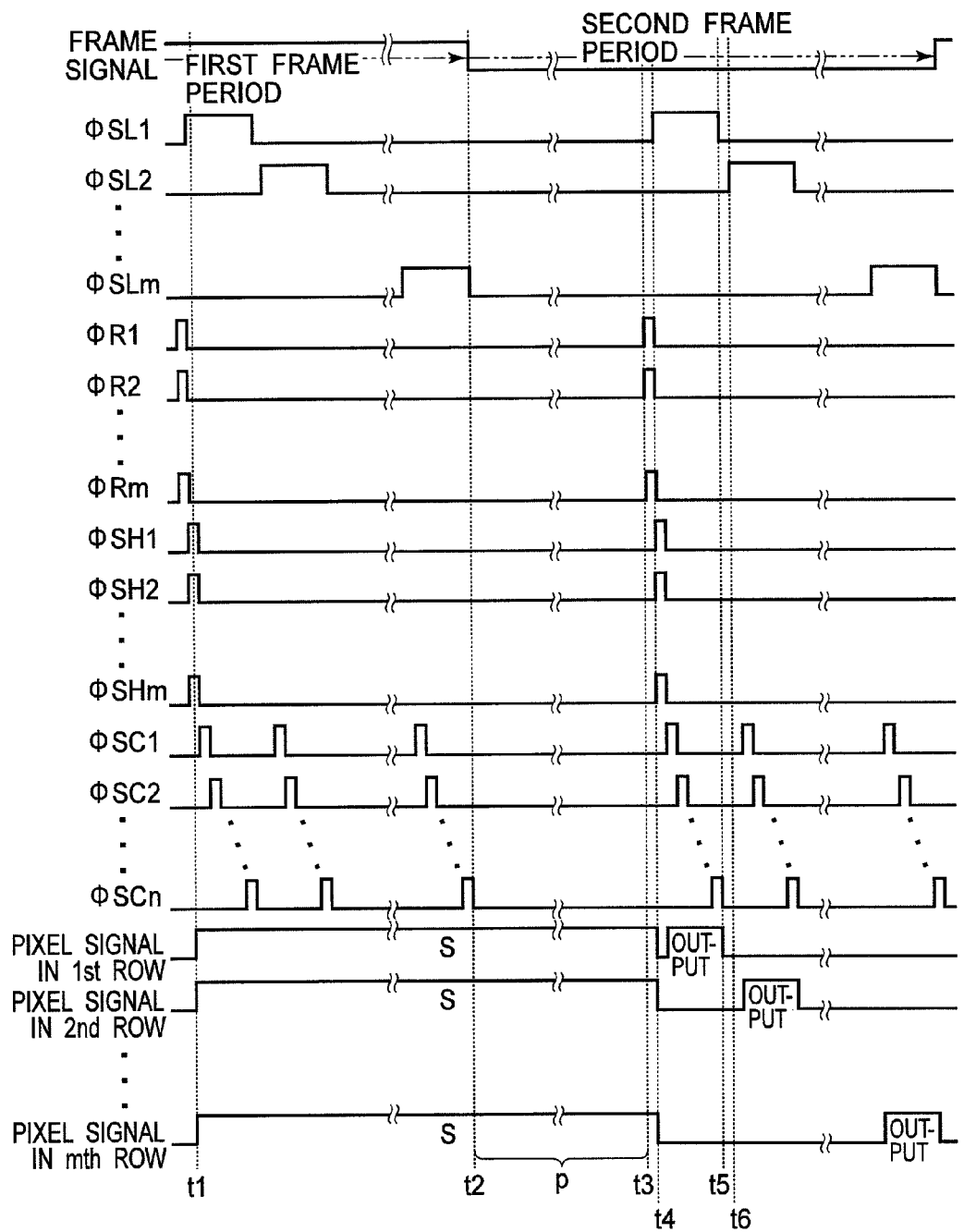
FIG. 6 is a timing chart illustrating the timing used to drive the imaging device to generate an image signal with global exposure.

Next, the operations of the imaging device 32 for generating an image signal using global exposure are described below with reference to FIG. 6.

At time t1 in the first period, the φSH for the first to mth rows, hereinafter referred to as φSH1 to φSHm, is simultaneously set to the high state, and then, the signal charges stored by the PDs 41 are transmitted to the FDs 42 in the pixels 40 in all the rows. After the transmission of the signal charges and after the φSH1 to φSHm are set to the low state, the PDs in all the pixels 40 in all rows start to generate and store signal charges.

At time t2 after outputting the pixel signals in the mth row in the first frame period, the first frame period comes to an end and the second frame period starts. At time t3, after a period has passed predetermined as sufficient for storing enough signal charges in the PDs 41 (refer to "p1"), the φR for the first to mth rows (refer to φR1 to φRm) are set to the high state, and then, the signal charges stored by the FDs 42 are swept to the Vdd, as in the line exposure method.

At time t4 after resetting the FDs 42 in all the pixels 40, the φSL1 is set to the high state and the row-selection transistors 46 in all the pixels 40 in the first row are switched on. By switching on the row-selection transistors 46 in the pixels 40 in the first row, the pixels signals are ready for output from the pixels 40 in the first row. As described below, the φSL1 is kept in the high state until pixels signals have been output from all the pixels in the first row.

In addition, at time t4, the φSH1 to φSHm are set to the high state, and then, the signal charge that is generated and stored by the PDs 41 between time t1 and time t4 (refer to "S" in the row of "pixel signal in the first to mth rows") are transferred to the FDs 42.

When the transfer of the signal charge to the FDs 42 completes, the φSC1 to φSCn are set to the high state one by one in order, and then the column-selection transistors 32cs in the first to nth columns are switched on one by one in order. Accordingly, all the pixel signals from the first to the nth columns in the first row are output from the imaging device 32 in order.

At time t5 after outputting the pixel signal generated by the pixel in the nth column in the first row, the φSL1 is set to the low state. At time t6, the φSL2 is set to the high state.

The φSH2 is kept in the low state while the φSL2 is kept in the high state, in contrast to the first row. Accordingly, the signal charges transferred at time t4 are stored by the FDs 42 even after time t6.

While the φSL2 is kept in the high state, the φSCs for all the columns are set to the high state one by one in order from the first column to the nth column, and then the column-selection transistors 32cs in the first to nth columns are switched on one by one in order, as in the first row. Accordingly, all the pixel signals between the first and nth columns in the second row are output from the imaging device 32 in order.

Thereafter, the φSL for the third to mth rows, hereinafter referred to as φSL3 to φSLm, are set to the high state in order. While the φSL3 to φSLm are set to the high state in order, the φSC1 to φSCn is set to the high state in order without transferring the signal charges to the FDs, as in the second row. Accordingly, all the pixel signals between the first and nth columns in the third to mth rows are output from the imaging device 32 in order.

In the above embodiment, a CMOS imaging device can be ordered to perform the global exposure or the line exposure according to the pattern of emitted illumination light used for capturing a subject.

As described above, it is preferable to order an entire light-receiving surface to simultaneously capture an optical image of a subject using pulsed white light because a user usually desires to photograph a quickly moving subject. In the above embodiment, the CMOS imaging device is ordered to perform the global exposure when the emission of the pulsed white light is detected. Accordingly, the distortion appearing in a captured image of a moving subject can be reduced.

On the other hand, as described above, when continuous light is used, it is preferable to reduce the influence of noise in the captured image. When a CMOS imaging device performs the global exposure, fixed pattern noise, such as a dark current, may increase, because it takes a long time to start reading pixel signals from pixels in some rows after having transferred the signal charges to the FDs 42. However, in the above embodiment, the CMOS imaging device is ordered to perform the line exposure when the emission of the continuous white light has been detected. Accordingly, the fixed pattern noise in an image can be reduced.

A CMOS imaging device is ordered to perform either the global exposure or the line exposure according to whether pulsed light or continuous light are detected, respectively, in the above embodiment. However, a benefit may also be obtained by selecting between global and line exposure on the basis of other possible patterns of emitted illumination light. If distortion appearing in an image of moving subject must be reduced, the global exposure should be carried out. On the other hand, if noise in an image must be reduced, the line exposure should be carried out.

Although the embodiments of the present invention have been described herein with reference to the accompanying drawings, obviously many modifications and changes may be made by those skilled in this art without departing from the scope of the invention.

The present disclosure relates to object matter contained in Japanese Patent Application No. 2007-315071 (filed on Dec. 5, 2007), which is expressly incorporated herein, by reference, in its entirety.

The invention claimed is:

1. An imaging-device driving unit that controls a CMOS imaging device mounted in an endoscope, comprising:
    a light source that emits illumination light;
    a light guide, provided in the endoscope and connected to the light source, having a first light guide branch and a second light guide branch, wherein the light guide splits into the first light guide branch and the second light guide branch within the endoscope, the first light guide branch directing the emitted illumination light from the light source to a subject;
    a light detector, provided in the endoscope and connected to the second light guide branch of the light guide, that detects a pattern of emitted illumination light from the light source, the CMOS imaging device being ordered to capture an optical image of the subject; and
    an exposure controller that orders the CMOS imaging device to perform a global exposure when the pattern of emitted illumination light detected by the light detector is a first pattern, and that orders the CMOS imaging device to perform a line exposure when the pattern of emitted illumination light detected by the light detector is a second pattern,
    wherein the light source emits pulsed light in the first pattern, and the light source emits continuous light in the second pattern.

2. An electronic endoscope, comprising:
    a CMOS imaging device;
    a light source that emits illumination light;
    a light guide, provided in the electronic endoscope and connected to the light source, having a first light guide branch and a second light guide branch, wherein the light guide splits into the first light guide branch and the second light guide branch within the electronic endoscope, the first light guide branch directing the emitted illumination light from the light source to a subject;
    a light detector, provided in the electronic endoscope and connected to the second light guide branch of the light guide, that detects a pattern of emitted illumination light from the light source, the CMOS imaging device being ordered to capture an optical image of the subject; and an exposure controller that orders the CMOS imaging device to perform a global exposure when the pattern of emitted illumination light detected by the light detector is a first pattern, and that orders the CMOS imaging device to perform a line exposure when the pattern of emitted illumination light detected by the light detector is a second pattern.

3. An endoscope system, comprising:
an endoscope having a CMOS imaging device;
a light source that emits illumination light;
a light guide, provided in the endoscope system and connected to the light source, having a first light guide branch and a second light guide branch, wherein the light guide splits into the first light guide branch and the second light guide branch within the endoscope, the first light guide branch directing the emitted illumination light from the light source to a subject;
a light detector, provided in the endoscope system and connected to the second light guide branch of the light guide, that detects a pattern of emitted illumination light from the light source, the CMOS imaging device being ordered to capture an optical image of the subject; and
an exposure controller that orders the CMOS imaging device to perform a global exposure when the pattern of emitted illumination light detected by the light detector is a first pattern, and that orders the CMOS imaging device to perform a line exposure when the pattern of emitted illumination light detected by the light detector is a second pattern.

4. An endoscope system, comprising:
an endoscope;
a CMOS imaging device;
a light source that includes:
   a lamp that emits illumination light,
   a rotary shutter that selectably blocks the emitted illumination light,
   a motor for rotating the rotary shutter, and
   a rotary shutter driving circuit for driving the motor;
a light guide, provided in the endoscope system and connected to the light source, having a first light guide branch and a second light guide branch, wherein the light guide splits into the first light guide branch and the second light guide branch within the endoscope, the first light guide branch that directs the emitted illumination light from the lamp to an object;
a diffusion lens disposed at an end of the first light guide branch of the endoscope;
an objective lens disposed at an end of the endo scope;
a light detector, provided in the endoscope system and connected to the second light guide branch of the light guide, that detects a pattern of emitted illumination light from the lamp, the CMOS imaging device being ordered to capture an optical image of the object; and
an exposure controller that orders the CMOS imaging device to perform a global exposure when the pattern of emitted illumination light detected by the detector is a first pattern, and that orders the CMOS imaging device to perform a line exposure when the pattern of emitted illumination light detected by the detector is a second pattern,
wherein light source emits pulsed light in the first pattern, and the light source emits continuous light in the second pattern.

* * * * *